United States Patent
Saito et al.

(10) Patent No.: US 6,894,001 B2
(45) Date of Patent: May 17, 2005

(54) FUNCTIONAL MATERIAL CONTAINING VOLATILE AGENT

(75) Inventors: Hidenao Saito, Fukui (JP); Koichi Taniguchi, Fukui (JP); Dazhong Wang, Fukui (JP)

(73) Assignee: Rengo Co., Ltd., Osaka (JP)

( * ) Notice: Subject to any disclaimer, the term of this patent is extended or adjusted under 35 U.S.C. 154(b) by 82 days.

(21) Appl. No.: 10/228,076

(22) Filed: Aug. 27, 2002

(65) Prior Publication Data

US 2003/0064648 A1 Apr. 3, 2003

(30) Foreign Application Priority Data

Aug. 27, 2001 (JP) ........................................ 2001-255529

(51) Int. Cl.[7] ............................................... B41M 5/30
(52) U.S. Cl. ........................ 503/205; 503/208; 503/209
(58) Field of Search ................................ 503/205, 208, 503/209

(56) References Cited

U.S. PATENT DOCUMENTS 4,717,710 A * 1/1988 Shimizu et al. ............. 503/213

FOREIGN PATENT DOCUMENTS

JP 62-179640 8/1987

* cited by examiner

*Primary Examiner*—Bruce Hess
(74) *Attorney, Agent, or Firm*—Wenderoth, Lind & Ponack, L.L.P.

(57) ABSTRACT

A functional material is proposed in which by developing colors, the degree of volatilization of a volatile agent can be visually checked, and the color is stabilized. A volatile agent having desensitizing property, a coloring agent, a developer and an embedding material are mixed while heating and melting, and retained on a carrier.

12 Claims, No Drawings

FUNCTIONAL MATERIAL CONTAINING VOLATILE AGENT

BACKGROUND OF THE INVENTION

This invention relates to a functional material which makes it possible to visually check the degree of volatilization of volatile agents.

As indicators for visually checking the end of effects by change in color, ones containing cobalt chloride retained in silica gel, ones in which a molten mixture comprising a volatile agent, an oil-soluble dye and an embedding material is retained in a porous carrier (U.S. Pat. No. 6,124,219), etc. are known.

The former changes color by absorbing moisture. The latter discolors with volatilization of the volatile agent.

But in either of them, since color changes gradually, differences among individuals develop in determining the end of effects, and it is sometimes difficult to clearly determine the end of effects.

In Japanese patent publication 62-179640, an indicator is a mothproofing agent and an organic electron-donative color compound and a developer coexist with a volatile mothproofing agent. This agent acts as a desensitizer. This indicator develops color quickly with volatilization of the volatile mothproofing agent. But after color has developed, it gradually fades. Thus, one may judge that color has not yet developed and keep using it in spite of the fact that the agent has volatilized.

An object of this invention is therefore to provide a functional material with which it is possible to visually check the degree of volatilization of a volatile agent by development of color, and after color has developed, the color is stable.

SUMMARY OF THE INVENTION

According to this invention, there is provided a functional material wherein a volatile agent having desensitizing property, a coloring agent, a developer and an embedding material are mixed while heating and melting and the mixture is retained on a carrier, whereby the degree of volatilization of the volatile agent can be visually checked.

Since a volatile agent having desensitizing property inhibits the reaction of the developer with the coloring agent, only after this volatile agent has volatilized to a certain degree, the coloring reaction takes place. Thus, it is possible to visually check the degree of volatilization of the volatile agent.

Since the embedding material is used, it is possible to keep the developed color from fading.

Further, by changing the weight ratio of the volatile agent to the developer in the range of 1:1 to 1000:1, it is possible to control the period until color develops.

DETAILED DESCRIPTION OF THE PREFERRED EMBODIMENT

This invention will be described below in detail.

The functional material according to this invention comprises a volatile agent having desensitizing property, a coloring agent, a developer, an embedding material and a carrier. Specifically, a volatile agent having desensitizing property, a coloring agent, a developer and an embedding material are mixed while heating and melting to prepare a volatile agent mixture, and the volatile agent mixture is retained on the carrier.

The volatile agent having desensitizing property (hereinafter simply referred to as "volatile agent") refers to one that inhibits reaction of a developer with a coloring agent and shows volatility at room temperature or when heated.

As such volatile agents, aromatics such as natural perfumes and synthetic perfumes; antibacterial agents such as allyl isothiocyanate and hinokitiol; pyrethroid such as empenthrin, benfluthrin and fenfluthrin; and other mothproofing agents such as *eucalyptus* oil, terpineol oil and peppermint oil, etc. may be used. By selecting some of them, functional materials having various functions can be obtained.

The developer refers to an agent which reacts with a coloring agent and causes it to develop color. As the developer, compounds having phenolic hydroxyl groups such as 2,2-bis(4'-hydroxyphenyl)propane (hereinbelow abbreviated to "BIS-A".), 2,2'-methylenebis(4-chlorophenol), 4,4'-bis(4-hydroxyphenyl)sulfone, pyrocatechol, methyl gallate and propyl p-hydroxybenzoate (hereinafter abbreviated to "HBP"), and acidic substances such as kaolin and talc may be used.

A coloring agent refers to an agent which changes its structure as a result of reaction with the developer and develops color. As a coloring agent, triphenylmethane phthalides such as malachite green and crystal violet lactone (hereinafter abbreviated to "CVL"); fluorans such as 2-N,N-dibenzylamino-6-diethylaminofluoran (hereinafter abbreviated to "G-DCF"), 3-cyclohexylamino-6-chlorofluoran; spiropyrans such as N-3,3-trimethylindolylbenzospiropyran, and 1,3,3-trimethylindoline-2,2-spiro-6'-nitro-8'-methoxybenzopyran; rhodamine lactams such as rhodamine B lactam and benzoyl leuco-methylene blue may be used.

The embedding material is a substance which is solid at normal temperature and compatible with the volatile agent when heated and melted. As the embedding material, mineral waxes represented by ozocerite; petroleum waxes such as paraffin wax and microcrystalline wax; natural waxes such as carnauba wax and rice wax; gum rosin, wood rosin, tall oil rosin, and their derivatives, and other chemicals such as stearyl alcohol, benzoic acid, 2,6-di-t-butyl-4-methylphenol, etc. may be used.

The content of the volatile agent in the volatile agent mixture is not specifically limited, but is preferably 1–95 wt %, more preferably 10–70 wt %. If less than 1 wt %, color may appear when the volatile agent mixture is prepared. If over 95 wt %, since the amount of the embedding material is insufficient, after color has appeared, it may gradually fade.

The content of the coloring agent in the volatile agent mixture is not particularly limited, but is preferably 0.01–5 wt %, more preferably 0.05–0.5 wt %. If less than 0.01 wt %, when color has appeared, it may be light. If over 5 wt %, color may appear when the volatile agent mixture is prepared.

The mixing ratio of the volatile agent to the developer is 1:1 to 1000:1, preferably 5:1 to 500:1 in weight ratio. If the weight ratio is less than 1:1, color may appear when the volatile agent mixture is prepared. If over 1000:1, since the amount of the developer in the volatile agent mixture is extremely small, color may be light even after the volatile agent has completely volatilized.

The content of the embedding material in the volatile agent mixture is not specifically limited, but is preferably 5–95 wt %, more preferably 10–80 wt %. If less than 5 wt %, after color has developed, color may gradually fade. If over 95 wt %, developed color may be light. Additionally the amount of the volatile agent mixture is larger than necessary. The functional material may be too large.

The volatile agent mixture may be prepared e.g. by melting the embedding material and mixing the volatile agent, coloring agent and developer thereto. The method of preparing the volatile agent mixture is not particularly limited.

The carrier is not specifically limited so long as it can retain the volatile agent mixture, but is preferably one that has a poor reactivity with the volatile agent, coloring agent and developer. As the carrier, polysaccharides such as cellulose and starch and their derivatives; natural polymer molecules such as collagen; synthetic polymer such as polyvinyl alcohol, polyurethane and polypropylene; inorganic substances such as silicate and silica gel, etc. may be used.

The carrier may be a particle or a sheet such as paper and nonwoven fabric.

As a method of retaining the volatile agent mixture to the carrier, any arbitrary one may be used. For example, if the carrier is a particle, the volatile agent mixture in a molten state may be impregnated into the carrier. If the carrier is a sheet, the volatile agent mixture may be applied with a brush, or coated with a die or roll coater.

Also, if the carrier is a sheet, the volatile agent mixture may be retained over the entire sheet or only on part of it. If it is retained only on part of the sheet, color develops only on this part, so that it is possible to contrast it with the unretained portion.

The color of the unretained portion is not particularly limited. For example, if the unretained portion is partially colored with the color in a predetermined state of volatilization, it is easy to judge that volatilization has become the predetermined state when the unretained portion has developed the same color.

By using the functional material according to this invention, it is possible to visually check the degree of volatilization of the volatile agent. If the amount of the developer used is small, it is possible to make color develop in a state in which volatilization of the volatile agent is near the end. Also, if the amount is large, it is possible to make color develop earlier in a state in which the amount of the volatile agent volatilized is small. Further, using this functional material, it is possible to visually check that a predetermined time has passed if use condition is stable.

EXAMPLES

Hereinbelow, by means of Examples and Comparative Examples, this invention will be described in more detail.

Example 1

200 parts by weight of citrus perfume as the volatile agent, 1 part by weight of CVL as the coloring agent, 2 parts by weight of BIS-A as the developer and 200 parts by weight of paraffin wax as the embedding material were kneaded while heating to prepare a volatile agent mixture.

2 g of the volatile agent mixture in a molten state was impregnated in 1 g of porous cellulosic beads (VISCOPEARL by Rengo Co., Ltd.) to obtain a functional material.

The functional material thus obtained was placed at room temperature, and the appeared color when the volatile agent had volatilized, and the color when it was placed for further three days were examined. The results are shown in Table 1.

Examples 2–5

Except that the volatile agents, coloring agents, developers, embedding materials and carriers shown in Table 1 were used, functional materials were prepared and examined in the same manner as in Example 1. The results are shown in Table 1.

Example 6

Except that filter paper (size: 90 mm×150 mm) was used in place of the cellulosic beads, a functional material was prepared and examined in the same manner as in Example 1.

Comparative Example 1

Except that no embedding material was used, a functional material was prepared and examined in the same manner as in Example 1.

With the functional material according to this invention, since the volatile agent having desensitizing property inhibits the reaction of the developer with the coloring agent, only after the volatile agent has volatilized to a certain degree, the coloring reaction takes place. Thus it is possible to visually check the degree of volatilization of the volatile agent.

Since the embedding material is used, it is possible to keep the developed color from fading.

Further, by changing the weight ratio of the volatile agent to the developer in the range of 1:1 to 1000:1, it is possible to control the period until color develops.

TABLE 1

| | | Volatile agent | Coloring agent | Developer | Embedding material | Carrier | Color of functional material | | |
|---|---|---|---|---|---|---|---|---|---|
| | | | | | | | Initial | After volatilation | 3 days later |
| Ex. | 1 | citrus perfume | CVL | BIS-A | paraffine wax | VISCOPEARL | white | purple | purple |
| | 2 | pyrethroid | CVL | BIS-A | paraffine wax | VISCOPEARL | white | purple | purple |
| | 3 | citrus perfume | G-DCF | BIS-A | paraffine wax | VISCOPEARL | white | green | green |
| | 4 | citrus perfume | CVL | HBP | paraffine wax | VISCOPEARL | white | purple | purple |
| | 5 | citrus perfume | CVL | BIS-A | stearyl alcohol | VISCOPEARL | white | purple | purple |
| | 6 | citrus perfume | CVL | BIS-A | paraffine wax | VISCOPEARL | white | purple | purple |
| Compara. Ex. | 1 | citrus perfume | CVL | BIS-A | None | VISCOPEARL | white | purple | white |

What is claimed is:

1. A functional material comprising a carrier, an embedding material retained on said carrier, and a volatile agent mixture comprising a volatile agent having a desensitizing property, a coloring agent, and a developer, wherein said volatile agent, said coloring agent and said developer are embedded in said embedding material such that said volatile agent inhibits any reaction between said coloring agent and said developer, and when said volatile agent vaporizes, said coloring agent and said developer react with each other, thereby coloring said coloring agent.

2. A functional material as claimed in claim 1 wherein the weight ratio of said embedding material to said volatile agent mixture is 5 to 95 wt %.

3. A functional material as claimed in claim 2 wherein said carrier is a particle.

4. A functional material as claimed in claim 2 wherein said carrier is a sheet and said volatile agent mixture is retained on at least part of said sheet.

5. A functional material as claimed in claim 4 wherein said sheet is a paper or a nonwoven fabric.

6. A functional material as claimed in claim 1 wherein the weight ratio of said volatile agent to said developer is 1:1 to 1000:1.

7. A functional material as claimed in claim 6 wherein said carrier is a particle.

8. A functional material as claimed in claim 6 wherein said carrier is a sheet and said volatile agent mixture is retained on at least part of said sheet.

9. A functional material as claimed in claim 8 wherein said sheet is a paper or a nonwoven fabric.

10. A functional material as claimed in claim 1 wherein said carrier is a particle.

11. A functional material as claimed in claim 1 wherein said carrier is a sheet and said volatile agent mixture is retained on at least part of said sheet.

12. A functional material as claimed in claim 11 wherein said sheet is a paper or a nonwoven fabric.

* * * * *